United States Patent
Salmond

[11] 3,945,960
[45] Mar. 23, 1976

[54] ANTIINFLAMMATORY AND ANALGESIC CYCLOALKANO-PYRIMIDIN-2(1H)-ONES

[75] Inventor: William G. Salmond, Kalamazoo, Mich.

[73] Assignee: Sandoz, Inc., E. Hanover, N.J.

[22] Filed: July 26, 1973

[21] Appl. No.: 382,721

[52] U.S. Cl. .......... 260/251 A; 260/566 F; 424/251
[51] Int. Cl.² ........................................ C07D 239/82
[58] Field of Search ................................ 260/251 A

[56] References Cited
UNITED STATES PATENTS
3,048,587  8/1962  Oroshnik .......................... 260/256.4
3,563,990  2/1971  Hardtmann .......................... 260/251

OTHER PUBLICATIONS
Salmond et al. (I) – C.A. 78, 111357b, (1973).
Salmond et al. (II) – C.A. 79, 78836c, (1973).

Primary Examiner—Raymond V. Rush
Attorney, Agent, or Firm—Gerald D. Sharkin; Richard E. Vila

[57] ABSTRACT
Anti-inflammatory and analgesic agents of the formula I:

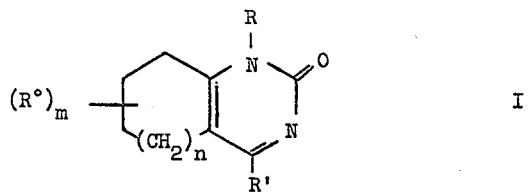

wherein $n$ is 2 to 7,
$R°$ is lower alkyl,
$m$ is 0, 1 or 2,
R is lower alkyl, alkenyl, cycloalkyl, cycloalkylalkyl or phenyl,
R' is a radical of the formula

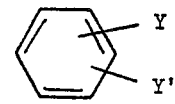

in which Y and Y' are the same or different and represent hydrogen, lower alkyl, lower alkoxy, halo of atomic weight of 19 to 36 or one of Y and Y' is trifluoromethyl while the other is hydrogen, or a radical of the formula

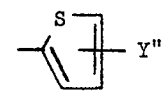

in which Y'' is hydrogen, fluorine, chlorine or alkyl of 1 to 3 carbon atoms, are prepared by cyclizing a compound of the formula II

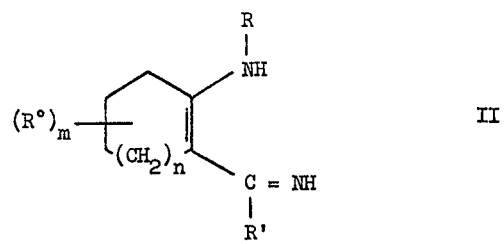

in which R, R', R°, m and n are as defined above, with, for example, phosgene.

12 Claims, No Drawings

ANTIINFLAMMATORY AND ANALGESIC CYCLOALKANO-PYRIMIDIN-2(1H)-ONES

This invention relates to $C_7$–$C_{12}$-cycloalkano-pyrimidin-2(1H)-one derivatives, to their preparation and intermediates useful in their preparation, and to pharmaceutical compositions and methods utilizing the pharmacological properties of said compounds.

The compounds of this invention have the formula I:

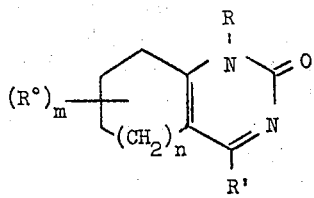
I wherein
$n$ is 2 to 7,
$R°$ is alkyl of 1 to 3 carbon atoms,
$m$ is 0, 1 or 2,
R is lower alkyl, preferably containing 1 to 5 carbon atoms, e.g., methyl, ethyl, isopropyl, butyl and isobutyl, alkenyl of 3 to 6 carbon atoms, cycloalkyl of 3 to 8 carbon atoms, cycloalkylalkyl of 4 to 10 carbon atoms in which the alkyl is of 1 to 3 carbon atoms and the cycloalkyl is of 3 to 8 carbon atoms, phenyl or substituted phenyl of the formula

in which Z and Z' which may be the same or different, represent hydrogen, halo of atomic weight of from 19 to 36, alkyl of 1 to 3 carbon atoms, alkoxy of 1 to 3 carbon atoms or trifluoromethyl,
R' is a radical of the formula

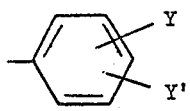

in which Y and Y' are the same or different and represent hydrogen, halo of atomic weight of 19 to 36, lower alkyl, preferably containing from 1 to 2 carbon atoms, e.g., methyl or ethyl, lower alkoxy, preferably containing from 1 to 2 carbon atoms, e.g., methoxy or ethoxy, or one of Y and Y' is trifluoromethyl while the other is hydrogen, or a radical of the formula

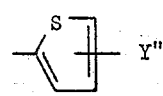

in which Y'' is hydrogen, fluorine, chlorine or alkyl of 1 to 3 carbon atoms.

The compounds of the formula I may be prepared by:
a. preparing a compound of the formula I, above, by cyclizing a compound of formula II

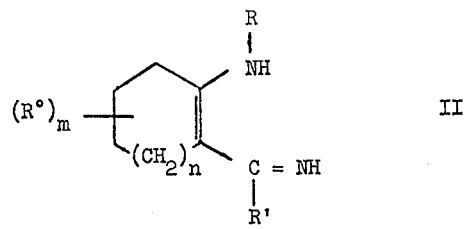
II in which R, R', R°, $m$ and $n$ are as defined above, with phosgene, b. preparing a compound of the formula Ia

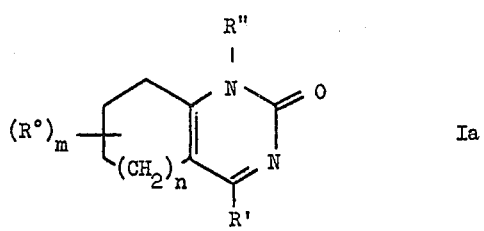
Ia in which R', R°, $m$ and $n$ are as defined above, and R'' has the same significance as R, defined above, except that it may not signify a tertiary alkyl group in which the tertiary carbon atom is directly attached to the ring nitrogen atom, by cyclizing a compound of formula IIa

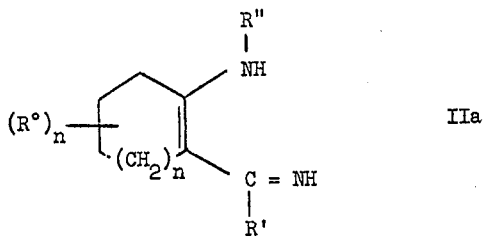
IIa wherein R°, R', R'', $m$ and $n$ are as defined above with a carbonic acid derivative selected from the group of
i. a $C_{1-2}$alkyl chlorocarbonate and
ii. a 1,1'-carbonyldiimidazole.

Process (a) is suitably carried out at a temperature of from −30°C. to +50°C., preferably −5°C. to 30°C. The reaction may be carried out in an organic solvent which is inert under the reaction conditions, suitably an aromatic hydrocarbon, e.g., benzene, toluene or xylene, preferably toluene. Other suitable solvents include dioxane. The mole ratio of the phosgene to the compound of formula II is not particularly critical, but a substantial excess of the phosgene is preferably employed. The process may optionally be carried out in the presence of an acid-binding agent such as an inorganic base, e.g., a trialkylamine or pyridine, preferably triethylamine. The reaction time may range for ½ to 10 hours, more usually 1 to 4 hours.

Process (b) (i) is suitably carried out at a temperature of from −30°C. to 100°C., preferably 0°C. to +30°C. The reaction may be carried out in an organic solvent which is inert under the reaction conditions, suitably an aromatic hydrocarbon, e.g., benzene, toluene or xylene, preferably toluene. Other suitable solvents include dioxane or the alkyl chlorocarbonate. The mole ratio of the chlorocarbonate to the compound of formula IIa is not particularly critical, but a substantial excess of the alkyl chlorocarbonate is preferably employed. The process may optionally be carried out in the presence of an acid-binding agent such as an inorganic base, e.g., a trialkylamine or pyridine, preferably triethylamine. The reaction time may range for ½ to 10 hours, more usually 1 to 4 hours.

Process b) (ii) is suitably carried out at a temperature of from 0°C. to 120°C., preferably 40°C. to 90°C. The reaction is preferably carried out in an organic solvent which is inert under the reaction conditions, suitably an aromatic hydrocarbon, e.g., benzene, toluene or xylene, especially benzene. An excess of 1,1'-carbonyldiimidazole is preferably employed.

The compounds of the formula I and Ia can be isolated from the reaction mixtures by working up by conventional procedures.

The compounds of formula II above can be prepared by reacting a compound of formula III

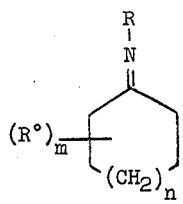    III in which R, R°, m and n are as defined above with a suitable strong base and a compound of formula IV

    IV in which R' is as defined above, in an inert solvent to form a solution of the Salt A

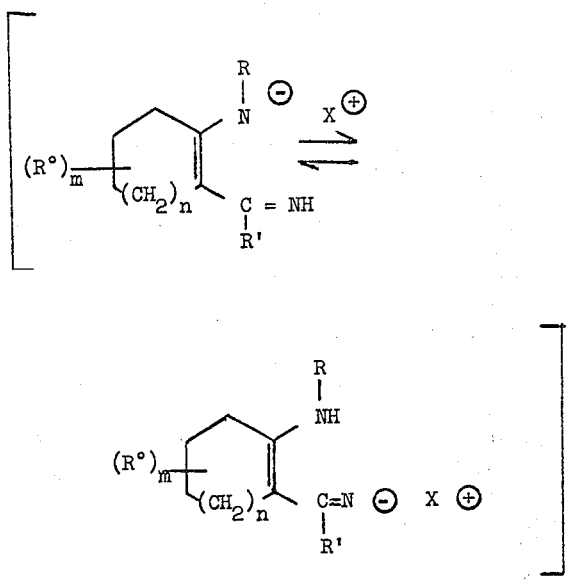    A in which R, R°, R', m and n are as defined above, and X is a metal, preferably lithium or magnesium, and quenching the solution with water.

Suitable strong bases are those which are capable of removing a hydrogen atom from the methylene group in the cycloalkane ring adjacent to the amine function of compound III to provide the desired anion for reaction with the compound of formula IV. They include the alkali metal salts, especially the lithium salt, of secondary amines such as diethylamine, dimethylamine and diisopropylamine, as well as other bases such as methyl magnesium iodide. Lithium diisopropylamide, because of its relatively large size, may be advantageous where there is an R° group in the 3- position of the compound of formula III since the formation of positional isomers may be alleviated. One mol of the strong base and up to about 1.2 mols can be used per mol of the compound of formula III, preferably equimolar amounts are used. The temperature of the reaction mixture is maintained at about 20°C. to 80°C.

Generally, the compound of formula III in a suitable solvent such as benzene, is added to a solution of the base in a suitable solvent and allowed to react to 20°C. to 150°C. The compound of formula IV, neat or in a suitable inert solvent, is then added to the reaction mixture of the base and compound III and reacted at 20°C. to 150°C. The compounds III and IV and the strong base may, however, be brought together simultaneously.

The resulting reaction mixture containing the salt of formula A can, at this point, be treated by process (a) or (b) above to yield directly the compound of formula I. Suitable temperature control should be exercised, as this reaction is more exothermic than when compound II is employed. However, the salt solution is advantageously quenched with water to obtain the compound of formula II, which can be reacted in situ according to process (a) or (b) to form compound I, but is preferably extracted and washed first using conventional methods.

The compounds of formula III can be prepared by reacting a compound of formula V

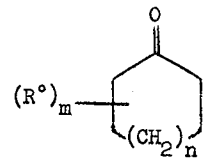    V wherein R°, m and n are as defined above, with a compound of formula VI

    VI wherein R is as defined above, in a known manner to eliminate one molecule of water, conveniently in the presence of a molecular sieve or a dehydrating agent, such as alumina, calcium chloride, phosphorus pentoxide or mixtures thereof. This reaction can be carried out at temperatures from 0° to about 80°C., conveniently 20° to 30°C. In cases where the compound of formula VI is volatile, an excess is generally mixed with the compound of formula V and the unreacted portion removed by vacuum distillation after removal of the dehydrating agent. When the compound of formula VI is non-volatile, equimolar proportions of compounds of formulae V and VI are mixed in suitable solvent such as benzene, the solvent then being removed in vacuo after completion of the reaction and after filtration of the dehydrating agent.

The compounds of formula V are known or can be produced in a known manner.

The compounds of formula I are useful because they possess pharmaceutical activity in animals. In particular, the compounds I are useful as anti-inflammatory agents as indicated by the Carrageenan-induced edema test in rates (15–150 mg./kg. p.o.). For the above-mentioned use, the dosage administered will, of course, vary depending upon known factors such as the particular compound used and mode of administration. However, in general, satisfactory results are obtained when administered orally at a daily dosage of from about 1.5 milligrams to about 200 milligrams per kilogram of body weight, preferably given in divided doses 2 to 4 times a day, or in sustained release form. For most mammals the administration of from about 120 milligrams to about 2000 milligrams of the compound per day provides satisfactory results and dosage forms suitable for internal administration comprise from about 30 milligrams to about 1000 milligrams of the compound in admixture with a solid or liquid pharmaceutical carrier or diluent.

The compounds of the formula I are also useful as analgesics as indicated by application of pressure to yeast-inflammed foot of the rat (15–150 mg./kg. p.o.). For such use, the compound may be administered to obtain satisfactory results in modes and forms similar to those employed in the treatment of inflammation and at dosages indicated above as applicable for the use of the compound in the treatment of inflammation.

For the above usage, oral administration with pharmaceutically acceptable carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents, and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g. magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixiers may contain the active ingredient in admixture with any of the conventional excipients utilized for the preparation of such compositions, e.g. suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of administration are solid compositions, particularly hard-filled capsules and tablets.

A representative formulation is a capsule prepared by conventional techniques and containing the following ingredients:

| Ingredient | Parts by Weight |
| --- | --- |
| Compound of formula I, e.g. 1-isopropyl-4-phenyl-6,7,8,9-tetrahydro-5H-cyclohepta[d]pyrimidin-2(1H)-one | 50 |
| Inert solid diluent, e.g., kaolin | 200 |

Preferred compounds of formula I, from the point of view of pharmacological activity, are those in which R signifies an isopropyl radical.

EXAMPLE 1

1-Isopropyl-4-Phenyl-5,6,7,8,9,10,11,12,13,14-decahydro-cyclododeca[d]pyrimidin-2(1H) -one.

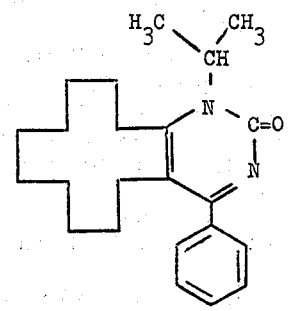

STEP A: Preparation of N-isopropylcyclododecylimine.

A mixture of 182 g. of cyclododecanone, 140 g. of isopropylamine, 5 g. of alumina, 5 g. of calcium chloride and 100 g. Linde Type 3A molecular sieves is allowed to stand for 4 days at room temperature, after which the solids are removed by filtration and the excess of isopropylamine is removed in vacuo at room temperature to obtain N-isopropylcyclododecylimine.

STEP B: 2-isopropylamino-α-phenyl-1-cyclododecene-1-methylenimine.

To n-butyl lithium (188 ml. of a 15% solution in hexane) is added a solution of 30 g. of diisopropylamine in 300 ml. benzene. After 15 minutes 67 g. of N-isopropylcyclododecylimine is added while stirring. After a further 45 minutes, 30 g. benzonitrile added dropwise and the mixture stirred for 45 minutes, producing a solution of the lithium salt of 2-isopropylamino-α-phenyl-1-cyclododecene-1-methylenimine. The reaction mixture is then treated with 20 ml. of water to obtain a solution of 2-isopropylamino-α-phenyl-1-cyclododecene-1-methyleneimine.

STEP C: 1-Isopropyl-4-phenyl-5,6,7,8,9,10,11,12,13,14-decahydrocyclododeca[d]pyrimidin-2(1H)-one.

To the solution of 2-isopropylamino-α-phenyl-1-cyclodecene-1-methylenimine obtained in Step B, above, at 0°C. is added 240 ml. of a 12.5% solution of phosgene in benzene. The reaction mixture is then flooded with water, the organic layer separated, dried and evaporated to an oil which is crystallized from diethyl ether/petroleum ether to obtain 1-isopropyl-4-phenyl-5,6,7,8,9,10,11,12,13,14-decahydro-cyclododeca[d]pyrimidine-2(1H)-one, m.p. 173°–176°C.

EXAMPLE 2

Following the procedure of Example 1 the following additional compounds of the invention are prepared:

A. 1-allyl-4-(4'-fluorophenyl)-5,6,7,8,9,10,11,12-octahydro-cyclodeca[d]pyrimidin-2(1H)-one.
B. 1-isopropyl-4-(2-thienyl)-5,6,7,8,9,10,11,12-octahydrocyclodeca[d]pyrimidin-2(1H)-one.
C. 1-isopropyl-4-(3',4'-dimethoxyphenyl)-5,6,7,8,9,10,11,12-octahydro-cyclodeca[d]pyrimidin-2(1H)-one.
D. 1-(3',4'-dimethoxylphenyl)-4-phenyl-5,6,7,8,9,10,11,12-octahydro-cyclodeca[d]pyrimidin-2(1H)-one.
E. 1-cyclopropylmethyl-4-phenyl-5,6,7,8,9,10,11,12-octahydrocyclodeca[d]pyrimidin-2(1H)-one.
F. 1-isopropyl-4-phenyl-5,6,7,8,9,10,11,12-octahydrocyclodeca[d]pyrimidin-2(1H)-one.
G. 1-isopropyl-4-phenyl-5,6,7,8,9,10,11,12-octahydro-cyclodeca[d]pyrimidin-2(1H)-one.
H. 1-cyclohexyl-4-phenyl-5,6,7,8,9,10,11,12-octahydrocyclodeca[d]pyrimidin-2(1H)-one.
I. 1-isopropyl-4-(4'-trifluoromethylphenyl)-5,6,7,8,9,10,11,12-octahydro-cyclodeca[d]pyrimidin-2(1H)-one.
J. 1-isopropyl-4-phenyl-6,7,8,9-tetrahydro-5H-cyclohepta[d]pyrimidin-2(1H)-one, m.p. 155°–157°C.
K. 1-cyclooctyl-4-phenyl-6,7,8,9-tetrahydro-5H-cyclohepta[d]pyrimidin-2(1H)-one, m.p. 78°–80°C.
L. 1-isopropyl-4-phenyl-5,6,7,8,9,10-tetrahydrocyclooocta[d]pyrimidin-2(1H)-one.
M. 1-isopropyl-4-phenyl-6,7,8,9,10,11-hexahydro-5H-cyclonona[d]pyrimidin-2(1H)-one.
M. 1-isopropyl-4-phenyl-6,7,8,9,10,11,12,13-octahydro-5H-cycloundeca[d]pyrimidin-2(1H)-one.
O. 1-cyclopropylmethyl-4-phenyl-5,6,7,8,9,10,11,12,13,14-decahydro-cyclododeca[d]pyrimidin-2(1H)-one.
P. 1-isopropyl-4-(4'-fluorophenyl)-5,6,7,8,9,10,11,12,13,14-decahydro-cyclododeca[d]pyrimidin-2(1H)-one.
Q. 1,4-diphenyl-5,6,7,8,9,10,11,12,13,14-decahydrocyclododeca[d]pyrimidin-2(1H)-one.
R. 1-(3',4'-dichlorophenyl)-4-phenyl-5,6,7,8,9,10,11,12,13,14-decahydro-cyclododeca[d]pyrimidin-2(1H)-one.
S. 1-isopropyl-8-methyl-4-phenyl-6,7,8,9-tetrahydro-5H-cyclohepta[d]pyrimidin-2(1H)-one.
T. 1-methallyl-8-methyl-4-phenyl-6,7,8,9-tetrahydra-5H-cyclohepta[d]pyrimidin-2(1H)-one.
U. 1-cyclopropylmethyl-8-methyl-4-phenyl-6,7,8,9-tetrahydro-5H-cyclohepta[d]pyrimidin-2(1H)-one.
V. 1-cyclopropyl-8-methyl-4-phenyl-6,7,8,9-tetrahydro-5H-cyclohepta[d]pyrimidin-2(1H)-one.
W. 1-(3',4'-dichlorophenyl)-4-phenyl-6,7,8,9-tetrahydro-5H-cyclohepta[d]pyrimidin-2(1H)-one.
X. 1-(4'-methylphenyl)-4-phenyl-6,7,8,9-tetrahydro-5H-cyclohepta[d]pyrimidin-2(1H)-one.
Y. 1-isopropyl-4-(2-thienyl)-6,7,8,9-tetrahydro-5H-cyclohepta[d]pyrimidin-2(1H)-one.

What is claimed is:

1. A compound of the formula:

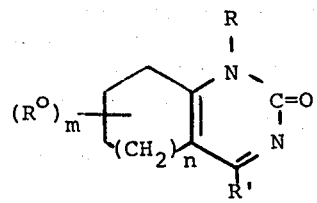

wherein
$n$ is 2 to 7,
$R°$ is alkyl of 1 to 3 carbon atoms,
$m$ is 0, 1 or 2.
$R$ is alkyl of 1 to 5 carbon atoms, cycloalkyl of 3 to 8 carbon atoms or cycloalkylalkyl of 4 to 10 carbon atoms in which the alkyl is of 1 to 3 carbon atoms and the cycloalkyl of 3 to 8 carbon atoms, and
$R'$ is a radical of the formula:

in which Y and Y' are independently hydrogen, fluoro, chloro, alkyl of 1 or 2 carbon atoms, alkoxy of 1 to 2 carbon atoms or one of Y and Y' is trifluoromethyl while the other is hydrogen, or a radical of the formula:

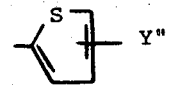

in which Y' is hydrogen, fluoro, chloro or alkyl of 1 to 3 carbon atoms.

2. A compound of claim 1 in which $n$ is 2.
3. A compound of claim 1 in which $n$ is 3.
4. A compound of claim 1 in which $n$ is 4.
5. A compound of claim 1 in which $n$ is 5.
6. A compound of claim 1 in which $n$ is 6.
7. A compound of claim 1 in which $n$ is 7.
8. The compound of claim 7 which is 1-isopropyl-4-phenyl-5,6,7,8,9,10,11,12,13,14-decahydro-cyclododeca[d]pyrimidin-2(1H)-one.
9. The compound of claim 2 which is 1-isopropyl-4-phenyl-6,7,8,9,-tetrahydro-5H-cyclohepta[d]pyrimidin-2(1H)-one.
10. The compound of claim 2 which is 1-cyclooctyl-4-phenyl-6,7,8,9-tetrahydro-5H-cyclohepta[d]pyrimidin-2(1H)-one.
11. A compound of claim 1 in which $R'$ is phenyl or substituted phenyl.
12. A compound of claim 1 in which $R$ is isopropyl.

* * * * *